(12) United States Patent
Becker et al.

(10) Patent No.: US 9,475,907 B2
(45) Date of Patent: Oct. 25, 2016

(54) PROCESS FOR THE PREPARATION OF POLYQUARTERNIUM-I

(71) Applicant: ALFRED E. TIEFENBACHER (GMBH & CO. KG), Hamburg (DE)

(72) Inventors: Stefan Becker, Hamburg (DE); Uwe Eilitz, Wolfen (DE); Gunnar Göthe, Wolfen (DE); Jens Flemming, Hamburg (DE)

(73) Assignee: Alfred E. Tiefenbacher GmbH & Co., KG, Hamburg (DE)

( * ) Notice: Subject to any disclaimer, the term of this patent is extended or adjusted under 35 U.S.C. 154(b) by 0 days.

(21) Appl. No.: 14/409,606

(22) PCT Filed: Jun. 19, 2013

(86) PCT No.: PCT/EP2013/001807
§ 371 (c)(1),
(2) Date: Dec. 19, 2014

(87) PCT Pub. No.: WO2013/189596
PCT Pub. Date: Dec. 27, 2013

(65) Prior Publication Data
US 2015/0197603 A1    Jul. 16, 2015

Related U.S. Application Data

(60) Provisional application No. 61/663,011, filed on Jun. 22, 2012.

(30) Foreign Application Priority Data

Jun. 22, 2012   (DE) ..................... 10 2012 012 263

(51) Int. Cl.
C08G 73/02     (2006.01)
A61L 12/14     (2006.01)
A61K 31/785    (2006.01)
C11D 3/37      (2006.01)

(52) U.S. Cl.
CPC ............. *C08G 73/02* (2013.01); *A61L 12/145* (2013.01); *C08G 73/0226* (2013.01)

(58) Field of Classification Search
CPC ...................................................... C08G 73/02
USPC ........................................................ 528/392
See application file for complete search history.

(56) References Cited

U.S. PATENT DOCUMENTS

| | | |
|---|---|---|
| 3,874,870 A | 4/1975 | Green et al. |
| 3,923,973 A | 12/1975 | Green et al. |
| 4,027,020 A | 5/1977 | Green et al. |
| 4,091,113 A | 5/1978 | Green et al. |
| 4,209,397 A | 6/1980 | Green et al. |
| 4,444,750 A | 4/1984 | Green et al. |
| 6,096,138 A | 8/2000 | Heiler et al. |
| 7,705,112 B2 * | 4/2010 | Yu ..................... C08G 73/0226 528/392 |

FOREIGN PATENT DOCUMENTS

| | | |
|---|---|---|
| DE | 2547774 A | 5/1976 |
| GB | 1521047 A | 8/1978 |
| WO | 2008131013 A1 | 10/2008 |
| WO | 2010124225 A1 | 10/2010 |

OTHER PUBLICATIONS

Search Report issued in DE 102012012263, dated Jan. 2, 2013 (3 pages).
International Search Report for PCT/EP2013/001807, dated Oct. 15, 2013 (4 pages).

* cited by examiner

*Primary Examiner* — Duc Truong
(74) *Attorney, Agent, or Firm* — Armstrong Teasdale LLP

(57) ABSTRACT

The present invention relates to a method for the preparation of polyquaternium-1, wherein an aprotic polar solvent is used as the reaction medium, and a solid polyquaternium-1 having a low degree of polydispersity.

9 Claims, No Drawings

US 9,475,907 B2

PROCESS FOR THE PREPARATION OF POLYQUARTERNIUM-I

CROSS-REFERENCE TO RELATED APPLICATIONS

This application is the §371 National Stage of International Application No. PCT/EP2013/001807, filed Jun. 19, 2013 which claims priority to German Application Serial No. 10 2012 012 263.2, filed Jun. 22, 2012 and U.S. Provisional Application Ser. No. 61/663,011, filed Jun. 22, 2012.

The present invention relates to a method for the preparation of poly[(dimethyl-imino)-2-butene-1,4-diyl chloride], α-[4-[tris(2-hydroxyethl)ammonium]-2-butenyl]-ω-[tris(2-hydroxyethyl)ammonium]-, dichloride, also known as polyquaternium-1, as well as a polyquaternium-1, which is obtainable as a solid substance having a low degree of polydispersity.

Polymeric quaternary ammonium compounds possess antimicrobial properties. Polyquaternium-1 is an antimicrobial substance, and it is marketed under the tradename Polyquad®. Polyquaternium-1 may be used as a preservative in eye drops and as liquid artificial tear substitutes. It is also used as a disinfectant for contact lenses.

The preparation of polyquaternium-1 comprises two method steps. In the first step the monomers trans-1,4-bis(dimethylamino)-2-butene and trans-1,4-dichloro-2-butene are reacted with each other, whereby a polymeric quaternary α,ω-dichloro-ammonium compound, i.e. poly[(dimethyl-imino)-2-butene-1,4-diyl chloride], α-(4-chloro-2-butenyl)-ω-chloro-, is obtained as a reaction product. In a second step, the terminal chlorine atoms are substituted by tris(2-hydroxyethyl)ammonium groups, whereby the polymeric quaternary α,ω-dichloroammonium compound is reacted with triethanolamine. In principle, two methods are applicable in order to carry out the aforementioned two-step synthesis. In the first method, the polycondensation reaction is carried out first, and subsequently the obtained polymeric quaternary α,ω-dichloroammonium compound is reacted with triethanolamine. In the second method, the polycondensation reaction is carried out in the presence of triethanolamine. Both methods are known in the state of the art. The prior art methods provide Polyquaternium-1 in the form of an aqueous solution.

DE 25 477 74 describes both, the one-step and the two-step method, for the preparation of polyquaternium-1. In the one-step method, trans-1,4-bis(dimethylamino)-2-butene and triethanolamine are concomitantly mixed with trans-1,4-dichloro-2-butene, whereby a ratio of approximately 1:1 between halogen equivalents and the total number of tertiary amine equivalents is used. The molar ratio of diamine and monoamine in the initial reaction mixture is about 2:1 to about 30:1. In the two-step method, trans-1,4-dichloro-2-butene is reacted with little less than one mol equivalent of trans-1,4-bis(dimethylamino)-2-butene in the first step. Under these reaction conditions the polycondensation reaction proceeds until the diamine is consumed. Due to the initial excess of dihalobutene relative to diamine in the reaction mixture, the polymeric chains possess terminal chlorine atoms. These are capable of reacting in a second step with triethanolamine. The polycondensation reaction and the reaction with triethanolamine are carried out in an aqueous solution, both in the one-step and the two-step method.

It has been observed in the methods described in DE 25 477 74 that the final reaction between the terminal chlorine atoms and triethanolamine was incomplete, so that the obtained polyquaternium-1 contained polymeric impurities, which could only be removed with great difficulties. Apart from polymers having a terminal chlorine atom, polymers having a terminal hydroxy group or a terminal butadienyl residue instead of the chlorine atom had been identified as impurities.

WO 2008/131013 suggests an improved method to synthesize polyquaternium-1, based on the one-step method, in which trans-1,4-bis(dimethylamino)-2-butene, triethanolamine and an acid are dissolved in water, whereafter trans-1,4-dichloro-2-butene is added to the solution. Hydrochloric acid, sulfuric acid and phosphoric acid are mentioned as examples of suitable acids.

WO 2010/124225 describes a process for preparing polyquaternium-1, which has a high average relative molecular weight of more than 28,000. The method described in WO 2010/124225 differs from that described in WO 2008/131013 merely by the fact that not the entire amounts of the triethanolamine and the acid were present in the initial reaction solution, and that the missing amounts were given into the reaction solution after the addition of trans-1,4-dichloro-2-butene.

In view of the above described state of the art the objective underlying the present invention was the provision of a further process for preparing polyquaternium-1, in which polymeric impurities are not formed. This objective has been achieved by the process as defined in the claims.

It has been found that water as a reaction medium can be omitted in the preparation of polyquaternium-1, based on the one-step method. The use of an aprotic polar solvent instead of water results in a polyquaternium-1, which does not contain any polymeric impurities. Accordingly the present invention pertains to a process for preparing polyquaternium-1, which comprises the steps of i) preparing a solution of trans-1,4-bis(dimethylamino)-2-butene and triethanolamine in an aprotic polar solvent, ii) adding trans-1,4-dichloro-2-butene to the solution obtained in step (i) in order to obtain a reaction mixture, and iii) isolating polyquaternium-1 from the reaction mixture obtained in step (ii).

The aprotic polar solvent is preferably a solvent with a relative permittivity ($\epsilon_r$) at 25° C. of at least 15, preferably 18 to 40, more preferably 20 to 30. The aprotic polar solvent may be selected from ketones, esters, nitriles, nitro compounds, tertiary carboxylic acid amides, urea derivatives, sulfoxides, sulfones, carbonate esters, and mixtures thereof. The aprotic polar solvent is preferably a ketone or an ester. Preferred aprotic polar solvents are acetone, γ-butyrolactone, dimethylformamide, N-methyl-2-pyrrolidone, acetonitrile, nitromethane, tetramethyl urea, dimethylsulfoxide, sulfolane and dimethyl carbonate. More preferable is acetone.

The molar ratio between trans-1,4-bis(dimethylamino)-2-butene and triethanolamine in the solution of step (i) is 5:1 to 1:1, preferably 3:1 to 1.5:1, and more preferably 2:1 to 1.6:1.

In step (ii) of the process according to the present invention, trans-1,4-dichloro-2-butene is added in an amount of 1.5 to 1 moles, preferably 1.4 to 1.05 moles, and more preferably 1.2 to 1.1 moles, per 1 mole of trans-1,4-bis(dimethylamino)-2-butene.

The temperature of the reaction solution in step (ii) of the method according to the present invention is usually adjusted to more than 20° C. and preferably ranges from 25° C. to 70° C., more preferably from 30° C. to 60° C., and most preferably from 35° C. to 55° C. As the case may be, the temperature of the reaction solution is to be set to a lower value when trans-1,4-dichloro-2-butene is added to the solution obtained in step (i) and ranges from 0° C. to 20° C., preferably from 5° C. to 18° C.

While the formed polyquaternium-1 remains in solution when water is used as the reaction medium, the method according to the present invention is particularly distinguished in that polyquaternium-1 precipitates from the reaction mixture when a certain degree of polymerization is reached, i.e. when a certain molecular weight is reached. According to a preferred embodiment of the present invention the reaction mixture in step (ii) is a solution from which the formed polyquaternium-1 precipitates. The precipitated polyquaternium-1 can be removed by filtration. Hence, a solid polyquaternium-1 is obtained.

The polyquaternium-1, which is formed in step (ii) of the method according to the present invention and which precipitates from the reaction solution when a certain degree of polymerization is reached, is distinguishable from a polyquaternium-1, which is formed in an aqueous medium and which does not precipitate from the reaction solution, by a narrower range of the molecular weight distribution, i.e. by a lower degree of polydispersity. The lower polydispersity can be explained by the fact that polyquaternium-1 precipitates from the reaction solution when a certain molecular weight is reached and, thus, is deprived of further chain elongation.

A polyquaternium-1 prepared according to the present invention has preferably an average relative molecular weight of 8,000 to 20,000, preferably 9,000 to 15,000, and more preferably from 10,000 to 12,000.

The method according to the present invention affords a polyquaternium-1 of high purity. This results from not using water as a reaction medium. The polymeric impurities known in the state of the art, which are described e.g. in WO 2008/131013 and WO 2010/124225, are presumably formed by reaction with hydroxide ions present in the aqueous reaction medium. It has also been found that other protic solvents, for example, methanol, ethanol, or isopropanol, support the formation of polymeric impurities in the reaction medium, either. For this reason, an aprotic polar solvent which is, in particular, free of water and other protic solvents, e.g. alcohols, is to be used in the process for preparing polyquatemium-1 according to the present invention.

The polyquatemium-1 according to the present invention can be used to manufacture pharmaceutical compositions or cleaning agent formulations, for example, eye drops, artificial tear solutions, and disinfectants, particularly for contact lenses.

EXAMPLES

The determination of the molecular weight and the purity grade were conducted by means of $^1$H-NMR: 400 MHz, $D_2O$.

Determination of the purity grade was also done by means of an HPLC analysis: Shimadzu CLASS-VP V6.12 SP5, column: Phenomenex BioSep-SEC-S2000 300×4.6, eluent (a) aqueous solution: 0.045 M $KH_2PO_4$, 0.45% NaCl, (b) acetonitrile, UV 205 & 228 nm.

Comparative Example

A solution of 2.0 g trans-1,4-bis(dimethylamino)-2-butene and 1.3 g triethanolamine dissolved in 4.7 ml isopropanol was prepared and cooled to 5° C. Then 1.9 g trans-1,4-dichloro-2-butene (98%) were added dropwise to the solution. The reaction mixture was warmed up to 20° C. to 40° C. and stirred at this temperature for approximately 20 minutes. The reaction mixture was then warmed up to 70° C. and stirred at this temperature for about 12 h. An orange-colored, clear oil was obtained, from which isopropanol was withdrawn in a rotary evaporator. An orange-colored resin including a white solid substance weighing 6.4 g was obtained. This product was a polyquaternium-1 with a molecular weight of approximately 9,000 and a purity grade of approximately 70%.

The experiment above was also carried out with ethanol (absolute) as the reaction medium, whereby 5.9 g polyquaternium-1 was obtained as an orange-colored foam with a molecular weight of approximately 9,000 and a purity grade of approximately 80%.

Example 1

To a solution of 4.0 g trans-1,4-bis(dimethylamino)-2-butene and 2.5 g triethanolamine dissolved in 50 ml acetone 3.9 g trans-1,4-dichloro-2-butene (98%) were added dropwise at a temperature of 18° C. (temperature of the solution). The reaction solution was warmed up to 40° C. and stirred at this temperature for 30 minutes, and thereafter for 12 h under reflux (oil bath temperature: 70° C.). The precipitated white solid substance was filtered and subsequently evaporated to dryness in a rotatory evaporator. 7.9 g of a pale yellow solid was obtained, which was a polyquaternium-1 with a molecular weight of approximately 10,000 and a purity grade of approximately 95%.

The invention claimed is:

1. Process for preparing poly[(dimethylimino)-2-butene-1,4-diyl-chloride], α-[4-[tris(2-hydroxyethyl)ammonium]-2-butenyl]-ω-[tris(2-hydroxyethyl)ammonium]-, dichloride (polyquaternium-1), wherein the process comprises the steps of:
   i) preparing a solution of trans-1,4-bis(dimethylamino)-2-butene and triethanolamine in an aprotic polar solvent,
   ii) adding trans-1,4-dichloro-2-butene to the solution obtained in step (i) in order to obtain a reaction mixture, and
   iii) isolating polyquaternium-1 from the reaction mixture obtained in step (ii).

2. Process according to claim 1, wherein the aprotic polar solvent has a relative permittivity ($\epsilon_r$) at 25° C. of at least 15.

3. Process according to claim 2, wherein the aprotic polar solvent is selected from ketones, esters, nitriles, nitro compounds, tertiary carboxylic acid amides, urea derivatives, sulfoxides, sulfones, carbonate esters, and mixtures thereof.

4. Process according to claim 3, wherein the aprotic polar solvent is selected from acetone, γ-butyrolactone, dimethylformamide, N-methyl-2-pyrrolidone, acetonitrile, nitromethane, tetramethyl urea, dimethylsulfoxide, sulfolane and dimethyl carbonate.

5. Process according to claim 1, wherein in step (i) the molar ratio between trans-1,4-bis(dimethylamino)-2-butene and triethanolamine in the solution is 5:1 to 1:1.

6. Process according to claim 1, wherein in step (ii) trans-1,4-dichloro-2-butene is added in an amount of 1.5 to 1 moles per 1 mole of trans-1,4-bis(dimethylamino)-2-butene.

7. Process according to claim 1, wherein in step (ii) the temperature of the reaction solution is adjusted to a value higher than 20° C.

8. Process according to claim 7, wherein in step (ii):
a) trans-1,4-dichloro-2-butene is added to the solution obtained in step (i) and the reaction solution has a temperature of 0° C. to 20° C., while the substance is being added, and
b) after completion of the addition the temperature of the reaction solution is adjusted to a value higher than 20° C.

9. Process according to claim 1, wherein the reaction mixture in step (ii) is a solution from which the formed polyquaternium-1 precipitates.

\* \* \* \* \*